(12) United States Patent
Booth et al.

(10) Patent No.: US 6,630,150 B1
(45) Date of Patent: Oct. 7, 2003

(54) SPHERONIZED SELF-EMULSIFYING SYSTEM FOR HYDROPHOBIC AND WATER-SENSITIVE AGENTS

(75) Inventors: Steven William Booth, Radlett (GB); Ashley Clarke, Royston (GB); John Michael Newton, London (GB)

(73) Assignee: Merck Sharp & Dohme Limited, Hertfordshire (GB)

(*) Notice: Subject to any disclaimer, the term of this patent is extended or adjusted under 35 U.S.C. 154(b) by 0 days.

(21) Appl. No.: 09/889,196

(22) PCT Filed: Nov. 1, 2000

(86) PCT No.: PCT/GB00/00150

§ 371 (c)(1),
(2), (4) Date: Oct. 15, 2001

(87) PCT Pub. No.: WO00/41676

PCT Pub. Date: Jul. 20, 2000

(30) Foreign Application Priority Data

Jan. 12, 1999 (GB) ............................................. 9900614
Jul. 2, 1999 (GB) ............................................. 9915584

(51) Int. Cl.[7] ........................ A61K 9/107; A61K 9/48; A61K 9/66; A61K 9/20
(52) U.S. Cl. ...................... 424/400; 424/451; 424/452; 424/455; 424/456; 424/464; 424/465
(58) Field of Search ............................ 424/400, 451, 424/452, 455, 456, 464, 465

(56) References Cited

FOREIGN PATENT DOCUMENTS

| EP | 0266323 A | * | 5/1988 |
| EP | 0266 323 | | 5/1988 |
| WO | WO 91/19563 | | 12/1991 |
| WO | WO 97/40702 | | 11/1997 |
| WO | WO 98/32443 | | 7/1998 |
| WO | WO9832443 A | * | 7/1998 |

OTHER PUBLICATIONS

F. Podczeck and J. M. Newton, J. Pharm. and Pharmacol., 46:82–85(1994).
F. Podczeck, *Pharmaceutical Power Compaction Technology*, Marcel Dekker Inc., New York, 1996, pp. 561–593.
P.H. Shipway and I.M. Hutchings, *Powder Technol.*, 76:23–30(1993).
F. Podczeck and J. M. Newton, *Int. J. Pharm.*, 124:253–259(1995).
F. Podczeck, *Particle–particle adhesion in Phamaceutical Powder Handling*, Imperial College Press, London, 1998, pp. 16–28.
Hans Fritz, et al.;*Magn. Res. Chem.*, 28:331–336(1990).

* cited by examiner

Primary Examiner—Carlos A. Azpuru
(74) Attorney, Agent, or Firm—David Rubin; David L. Rose

(57) ABSTRACT

A self-emulsifying system comprises i) microcrystalline cellulose and ii) an oily substance, surfactant, and water is useful for providing solid dosage forms of hydrophobic or water sensitive agents when dried or extruded and spheronized.

14 Claims, 7 Drawing Sheets

| Formulation number* | lactose: Avicel (%) | MP: water (%) | Mass of MPW (g) | Mass of MP (g) | Extrusion force (kN) |
|---|---|---|---|---|---|
| 1.1 | 0:100 | 46:54 | 39.962 | 18.38 | 13.6 |
| 2.1 | 12.75:87.5 | 46:54 | 42.980 | 19.77 | 6.7 |
| 2.2 | 12.75:87.5 | 46:54 | 40.923 | 18.83 | 8.0 |
| 2.3 | 12.75:87.5 | 46:54 | 37.983 | 17.47 | 11.3 |
| 3G.1 | 25:75 | 46:54 | 33.036 | 15.20 | 12.9 |
| 4.1 | 37.5:62.5 | 46:54 | 32.976 | 15.17 | 8.9 |
| 4.2 | 37.5:62.5 | 46:54 | 29.962 | 13.78 | 12.9 |
| 5.1 | 50:50 | 46:54 | 27.810 | 12.79 | 10.2 |
| 5.2 | 50:50 | 46:54 | 26.777 | 12.32 | 11.7 |
| 6.1 | 25:75 | 0:100 | 42.992 | 0 | 4.6 |
| 6.2 | 25:75 | 0:100 | 40.012 | 0 | 6.3 |
| 6.3 | 25:75 | 0:100 | 38.016 | 0 | 9.3 |
| 6.4 | 25:75 | 0:100 | 36.050 | 0 | 10.7 |
| 7.1 | 25:75 | 23:77 | 37.987 | 8.74 | 8.7 |
| 8.1 | 25:75 | 69:31 | 31.916 | 22.02 | 13.7 |
| 9.1 | 25:75 | 92:8 | 30.746 | 28.29 | 17.8 |
| 9.2 | 25:75 | 92:8 | 33.527 | 30.85 | 14.8 |
| 10i.1 | 5:95 | 12:88 | 51.324 | 6.16 | 5.6 |
| 10i.2 | 5:95 | 12:88 | 48.960 | 5.88 | 6.4 |
| 10i.3 | 5:95 | 12:88 | 47.238 | 5.67 | 7.8 |
| 10i.4 | 5:95 | 12:88 | 44.104 | 5.29 | 11.1 |
| 11i.1 | 5:95 | 80:20 | 38.986 | 31.19 | 11.8 |
| 12i.1 | 45:55 | 12:88 | 30.133 | 3.62 | 9.7 |
| 12i.2 | 45:55 | 12:88 | 31.987 | 3.84 | 7.1 |
| 13i.1 | 45:55 | 80:20 | 27.128 | 21.70 | 16.4 |

*Batches chosen for analysis in bold.

Table 1.

| Formulation number* | lactose: Avicel (%) | MP: water (%) | Mass of MPW (g) | Mass of MP (g) | Extrusion force (kN) |
|---|---|---|---|---|---|
| 1.1 | 0:100 | 46:54 | 39.962 | 18.38 | 13.6 |
| 2.1 | 12.75:87.5 | 46:54 | 42.980 | 19.77 | 6.7 |
| 2.2 | 12.75:87.5 | 46:54 | 40.923 | 18.83 | 8.0 |
| 2.3 | 12.75:87.5 | 46:54 | 37.983 | 17.47 | 11.3 |
| 3G.1 | 25:75 | 46:54 | 33.036 | 15.20 | 12.9 |
| 4.1 | 37.5:62.5 | 46:54 | 32.976 | 15.17 | 8.9 |
| 4.2 | 37.5:62.5 | 46:54 | 29.962 | 13.78 | 12.9 |
| 5.1 | 50:50 | 46:54 | 27.810 | 12.79 | 10.2 |
| 5.2 | 50:50 | 46:54 | 26.777 | 12.32 | 11.7 |
| 6.1 | 25:75 | 0:100 | 42.992 | 0 | 4.6 |
| 6.2 | 25:75 | 0:100 | 40.012 | 0 | 6.3 |
| 6.3 | 25:75 | 0:100 | 38.016 | 0 | 9.3 |
| 6.4 | 25:75 | 0:100 | 36.050 | 0 | 10.7 |
| 7.1 | 25:75 | 23:77 | 37.987 | 8.74 | 8.7 |
| 8.1 | 25:75 | 69:31 | 31.916 | 22.02 | 13.7 |
| 9.1 | 25:75 | 92:8 | 30.746 | 28.29 | 17.8 |
| 9.2 | 25:75 | 92:8 | 33.527 | 30.85 | 14.8 |
| 10i.1 | 5:95 | 12:88 | 51.324 | 6.16 | 5.6 |
| 10i.2 | 5:95 | 12:88 | 48.960 | 5.88 | 6.4 |
| 10i.3 | 5:95 | 12:88 | 47.238 | 5.67 | 7.8 |
| 10i.4 | 5:95 | 12:88 | 44.104 | 5.29 | 11.1 |
| 11i.1 | 5:95 | 80:20 | 38.986 | 31.19 | 11.8 |
| 12i.1 | 45:55 | 12:88 | 30.133 | 3.62 | 9.7 |
| 12i.2 | 45:55 | 12:88 | 31.987 | 3.84 | 7.1 |
| 13i.1 | 45:55 | 80:20 | 27.128 | 21.70 | 16.4 |

*Batches chosen for analysis in bold.

Table 2.

| Formulation number* | Size fractions (μm) | | | | | | | | |
|---|---|---|---|---|---|---|---|---|---|
| | <500 | 500-710 | 710-1000 | 1000-1400 | 1400-2000 | 2000-2800 | 2800-4000 | 4000-5600 | >5600 |
| 1.1 | 0 | 0.020 | 0.181 | 16.992 | 27.478 | 0.005 | 0 | 0 | 0 |
| 2.1 | 0 | 0.012 | 0.052 | 0.386 | 3.711 | 9.441 | 11.248 | 9.521 | 10.410 |
| 2.2 | 0.041 | 0.060 | 0.205 | 7.132 | 16.710 | 10.172 | 3.155 | 1.159 | 6.598 |
| 2.3 | 0 | 0.016 | 0.440 | 24.039 | 20.439 | 0.023 | 0 | 0 | 0 |
| 3G.1 | 0 | 0.045 | 0.433 | 22.408 | 22.537 | 0 | 0 | 0 | 0 |
| 4.1 | 0.086 | 0.155 | 0.338 | 4.665 | 14.468 | 11.730 | 5.840 | 2.656 | 8.379 |
| 4.2 | 0 | 0.090 | 0.738 | 26.228 | 19.928 | 0.033 | 0 | 0 | 0 |
| 5.1 | 0 | 0 | 0.298 | 25.385 | 21.474 | 0.167 | 0.033 | 0.112 | 0 |
| 5.2 | 0 | 0.038 | 0.611 | 27.400 | 19.185 | 0.074 | 0 | 0 | 0 |
| 6.1 | 0.009 | 0.008 | 0.003 | 0.010 | 0.094 | 11.515 | 22.368 | 0.970 | 0 |
| 6.2 | 0.049 | 0.030 | 0.066 | 2.345 | 13.989 | 8.550 | 1.872 | 2.709 | 0.690 |
| 6.3 | 0.347 | 4.058 | 23.889 | 5.518 | 0.692 | 0.497 | 0 | 0 | 0 |
| 6.4 | 0.390 | 6.532 | 22.499 | 1.593 | 0.061 | 0 | 0 | 0 | 0 |
| 7.1 | 0 | 0.051 | 1.993 | 36.090 | 1.169 | 0.008 | 0 | 0 | 0 |
| 8.1 | 0.024 | 0.035 | 0.338 | 22.389 | 29.592 | 0.034 | 0 | 0 | 0 |
| 9.1 | 0.669 | 1.969 | 8.154 | 19.651 | 7.220 | 4.229 | 0 | 0 | 0 |
| 9.2 | 0.080 | 0.021 | 0.099 | 8.918 | 31.377 | 7.248 | 0 | 0 | 0 |
| 10i.1 | 0.005 | 0.007 | 0.016 | 1.108 | 12.766 | 16.106 | 3.094 | 0 | 0 |
| 10i.2 | 0.079 | 0.132 | 0.492 | 3.570 | 11.806 | 10.091 | 2.487 | 2.394 | 2.129 |
| 10i.3 | 0.249 | 0.812 | 5.575 | 10.972 | 6.828 | 1.503 | 0.854 | 3.885 | 2.328 |
| 10i.4 | 0.324 | 3.365 | 24.118 | 5.977 | 0.006 | 0 | 0 | 0 | 0 |
| 11i.1 | 0.036 | 0.026 | 0.343 | 21.784 | 26.767 | 0.015 | 0 | 0 | 0 |
| 12i.1 | 0.030 | 1.128 | 21.061 | 17.296 | 0.162 | 0 | 0 | 0 | 0 |
| 12i.2 | 0.113 | 0.286 | 1.711 | 14.675 | 15.737 | 3.159 | 1.069 | 2.144 | 0 |
| 13i.1 | 0.128 | 0.053 | 4.448 | 7.079 | 33.085 | 6.510 | 0 | 0 | 0 |

* Batches chosen for analysis in bold.

Table 3.

| Formulation number | median diameter (μm) | spread (μm) | size fraction mode value | % in modal fraction |
|---|---|---|---|---|
| 1.1 | 1524 | 1000 | 1400-2000 | 61.5 |
| 2.3 | 1365 | 1290 | 1000-1400 | 53.5 |
| 3G.1 | 1397 | 1290 | 1400-2000 | 49.6 |
| 4.2 | 1349 | 1290 | 1000-1400 | 55.8 |
| 5.2 | 1333 | 1290 | 1000-1400 | 57.9 |
| 6.4 | 810 | 1050 | 710-1000 | 72.4 |
| 7.1 | 1190 | 1290 | 1000-1400 | 91.8 |
| 8.1 | 1460 | 1000 | 1400-2000 | 56.5 |
| 9.1 | 1206 | 2450 | 1000-1400 | 46.9 |
| 10i.4 | 857 | 900 | 710-1000 | 71.4 |
| 11i.1 | 1444 | 1000 | 1400-2000 | 54.7 |
| 12i.1 | 968 | 900 | 710-1000 | 53.1 |
| 13i.1 | 1651 | 2090 | 1400-2000 | 64.5 |

Table 4.

| Formulation number | Disintegration time (min) | s.d. |
|---|---|---|
| 1.1 | 8.04 | 1.16 |
| 2.3 | 4.94 | 0.85 |
| 3G.1 | 5.95 | 1.22 |
| 4.2 | 7.65 | 2.33 |
| 5.2 | 7.22 | 2.65 |
| 6.4 | 94.65 | 13.96 |
| 7.1 | 10.58 | 2.46 |
| 8.1 | 3.58 | 0.76 |
| 9.1 | 3.04 | 1.34 |
| 10i.4 | 23.82 | 14.38 |
| 11i.1 | 5.52 | 2.55 |
| 12i.1 | 15.37 | 3.48 |
| 13i.1 | 6.57 | 2.11 |

Table 5.

| Formulation number | 710-1000 μm | | 1000-1400 μm | |
|---|---|---|---|---|
| | load (kg) | s.d. | load (kg) | s.d. |
| 1.1 | 0.103* | 0.020 | 0.191 | 0.024 |
| 2.3 | 0.086 | 0.013 | 0.195 | 0.029 |
| 3G.1 | 0.092 | 0.010 | 0.193 | 0.014 |
| 4.2 | 0.072 | 0.012 | 0.166 | 0.027 |
| 5.2 | 0.075 | 0.011 | 0.152 | 0.019 |
| 6.4 | 1.723 | 0.228 | 1.888 | 0.939 |
| 7.1 | 0.236 | 0.067 | 0.492 | 0.085 |
| 8.1 | 0.027* | 0.003 | 0.039* | 0.004 |
| 9.1 | 0.004* | 0.001 | 0.010* | 0.003 |
| 10i.4 | 0.551 | 0.121 | 0.724 | 0.069 |
| 11i.1 | 0.009* | 0.003 | 0.016* | 0.003 |
| 12i.1 | 0.461 | 0.080 | 0.674 | 0.130 |
| 13i.1 | 0.017* | 0.005 | 0.023* | 0.006 |

*Deforming pellets

Table 6.

| Formulation number | 710-1000 μm | | 1000-1400 μm | |
|---|---|---|---|---|
| | Ecc | s.d. | Ecc | s.d. |
| 1.1 | 0.5134 | 0.1413 | 0.6286 | 0.1027 |
| 2.3 | 0.5209 | 0.1490 | 0.5991 | 0.1047 |
| 3G.1 | 0.5047 | 0.1140 | 0.6253 | 0.1016 |
| 4.2 | 0.5594 | 0.1333 | 0.6052 | 0.1016 |
| 5.2 | 0.5326 | 0.1301 | 0.6054 | 0.09096 |
| 6.4 | 0.5574 | 0.1747 | 0.5141 | 0.1987 |
| 7.1 | 0.5446 | 0.1214 | 0.5892 | 0.1126 |
| 8.1 | 0.5363 | 0.1287 | 0.6219 | 0.08769 |
| 9.1 | 0.5048 | 0.1334 | 0.5296 | 0.1191 |
| 10i.4 | 0.6252 | 0.1101 | 0.6416 | 0.1050 |
| 11i.1 | 0.5238 | 0.1306 | 0.5904 | 0.1068 |
| 12i.1 | 0.5629 | 0.1195 | 0.6070 | 0.1222 |
| 13i.1 | 0.5219 | 0.1275 | 0.5438 | 0.1079 |

Table 7.

| Formulation number | Rtm (µm) | s.d. | N |
|---|---|---|---|
| 1.1 | 10.09 | 1.44 | 3 |
| 2.3 | 10.85 | 1.29 | 4 |
| 3G.1 | 10.86 | 1.30 | 5 |
| 4.2 | 13.57 | 1.74 | 4 |
| 5.2 | 13.36 | 1.67 | 4 |
| 6.4 | 14.50 | 0.73 | 3 |
| 7.1 | 11.47 | 0.63 | 3 |
| 8.1 | 9.24 | 1.52 | 4 |
| 9.1 | 15.36 | 1.19 | 5 |
| 10i.4 | 12.90 | 1.61 | 4 |
| 11i.1 | 8.49 | 0.81 | 5 |
| 12i.1 | 14.47 | 1.74 | 5 |
| 13i.1 | 8.73 | 1.35 | 4 |

N: number of observations

SPHERONIZED SELF-EMULSIFYING SYSTEM FOR HYDROPHOBIC AND WATER-SENSITIVE AGENTS

This application is a 371 of International Application Number PCT/GB00/00150, and claims the benefit of GB 9900614.0, filed Jan. 12, 1999, and GB 9915584.8, filed Jul. 2, 1999.

BACKGROUND OF THE INVENTION

The present invention relates to mixtures suitable for formulating hydrophobic and water-sensitive active agents, these mixtures when dried, processes for producing dosage forms from the mixtures in the wet or dry states and the dosage forms themselves.

Self-emulsifying drug delivery systems have been shown to be a method of increasing the bioavailability of poorly water soluble active agents, such as drugs, and are an alternative to traditional formulations of lipophilic active agents.

A self-emulsifying system is a mixture of oil and surfactant which forms a fine oil-in-water emulsion when introduced into an aqueous phase under conditions of gentle agitation. Such mixtures can be used as, for example, pharmaceutical oral drug delivery systems for lipophilic compounds by dissolving the drug in the oil phase. The system is expected to self-emulsify rapidly in the aqueous contents of the stomach, thereby presenting the drug in solution in small droplets of oil. The gentle agitation required for the emulsification is provided by the digestive motility of the stomach. Fine oil droplets should empty rapidly from the stomach and promote wide distribution of the drug throughout the gastrointestinal tract, thereby minimising irritation frequently encountered with extended contact between bulk drug substances and the gut wall. The self-emulsifying drug delivery systems also provide a large interfacial area across which the drug can diffuse into the gastrointestinal fluids. Since the drug is dissolved in the oil phase the dissolution step, which can be absorption rate limiting for poorly water soluble drugs, is eliminated.

Several combinations of oil and surfactant have been used to produce self-emulsifying systems. The ingredients most frequently used are medium chain triglyceride oils (vegetable oils) and nonionic surfactants, which are acceptable for oral ingestion. Factors affecting the efficiency of a self-emulsifying system are the HLB and concentration of the surfactant. The dosage forms which result from these systems are usually either liquids or hard or soft gelatin capsules.

SUMMARY OF THE INVENTION

A self-emulsifying system comprises i) microcrystalline cellulose and ii) an oily substance, surfactant, and water is useful for providing solid dosage forms of hydrophobic or water sensitive agents when dried or extruded and spheronised.

BRIEF DESCRIPTION OF THE DRAWINGS

FIG. 1 is a table (Table 1) that tabulates the quantities of liquid incorporated and the steady state extrusion force.

FIG. 2 is a table (Table 2) that tabulates the formulation number and the size fractions.

FIG. 3 is a table (Table 3) that tabulates the results of the size analysis of the formulations.

FIG. 4 is a table (Table 4) that tabulates the disintegration time for the formulations.

FIG. 5 is a table (Table 5) that tabulates the crushing load in size fractions.

FIG. 6 is a table (Table 6) that tabulates the shape factors for the formulation pellets.

FIG. 7 is a table (Table 7) that tabulates the surface roughness for the formulations.

DETAILED DESCRIPTION OF THE INVENTION

The present invention provides a self-emulsifying system which comprises:

I. a first portion comprising microcrystalline cellulose; and

II. a second portion comprising:
   (A) up to 200%, based on the weight of the first portion, of an oily substance;
   (B) between 2 and 100%, based on the weight of the first portion, of a surfactant; and
   (C) between 2 and 1000%, based on the weight of the oily substance and the surfactants, of water;
   wherein the total weight of the oily substance and the surfactant is between 2 and 200% of the first portion.

Microcrystalline cellulose is commercially available, for example under the name Avicel®. The term includes, but is not limited to, pharmaceutical grade microcrystalline cellulose as defined in the British Pharmacopeia. Various grades of microcrystalline cellulose are described in the Handbook of Pharmaceutical Excipients, $2^e$, ed. by Wade and Weller, 1994, London and Washington, pages 84 to 87. As an alternative to microcrystalline cellulose powdered cellulose may be used.

Again, the powdered cellulose may be, but is not limited to, pharmaceutical grade. A description of various grades can be found in the above reference at pages 88–90.

The oily substance generally comprises a fatty acid ester or a long chain saturated, partially unsaturated or unsaturated long chain hydrocarbon. Thus the oily substance is preferably a $C_{1-20}$ ester of a $C_{6-30}$ acid or a $C_{20-100}$ hydrocarbon or a mixture thereof.

The $C_{6-30}$ acid may be naturally occurring or synthetic and generally contains one, two, three, four or more double bonds, particularly one, two or three double bonds, and may be substituted with one or more hydroxy groups. The $C_{1-20}$ ester is the residue of a $C_{1-20}$ alcohol comprising one, two or three hydroxy groups, which alcohol may be naturally occurring or synthetic. The acid and ester are generally linear or branched but may contain cyclic portions.

The $C_{20-100}$ hydrocarbon is unsaturated, partially saturated or saturated, and is preferably saturated. It may be linear or branched or contain cyclic portions but is preferably linear. It preferably contains 30–80 carbon atoms.

Examples of fatty acids include, but are not limited to, caproic acid, capric acid, caprylic acid, oleic acid, palmoic acid, stearic acid, linoleic acid, octanoic acid, decanoic acid, linolenic acid, palmitic acid, palmitoleic acid, arachidic acid, myristic acid, behenic acid and lignic acid. Mono, di and tri glycerides of these fatty acids are favoured, in particular medium chain mono and diglycerides. Capric acid and caprylic acid are favoured. Naturally occurring vegetable oils such as soyabean oil may be used.

Examples of $C_{20-100}$ hydrocarbon are various grades of paraffin.

The surfactant may be any known surfactant which reduces the surface tension of the water or the oily substance thus facilitating mixing. The surfactant may be cationic, anionic, non-ionic or amphoteric. A particularly favoured surfactant is polysorbate 80, generally used at 15–50% w/w. A mixture of surfactants may be used such as polysorbate 80 and span 80. Span 80 is generally used at 5–25% w/w.

The amount of oily substance present is preferably up to 90%, particularly between 5 and 80%, more particularly between 10 and 50%, especially between 20 and 42% of the weight of the first portion.

The amount of surfactant present is preferably between 10 and 90%, particularly between 20 and 80%, and more particularly between 20 and 50% of the weight of the first portion.

The amount of water present is preferably between 2 and 150%, more preferably between 2 and 100%, particularly between 3 and 80%, more particularly between 5 and 60% and especially between 8 and 42% of the weight of oil and surfactant.

The combined weight of the second portion is preferably between 30 and 95% and particularly between 35 and 95% by weight of the first portion and especially between 40 and 90%.

The precise quantities of surfactant, oily substance and water which may be present will depend on the particular nature of these substances.

Specific combinations of oil and surfactant that may be used are: mono and diglycerides USNF (50% w/w) and polysorbate 80 NF (50% w/w); mono and diglycerides USNF (70% w/w), polysorbate 80 NF (20% w/w) and span 80 (10% w/w); and soyabean oil (30%) w/w, polysorbate 80 NF (49% w/w) and span 80 (21% w/w).

The optimal quantities for forming a dosage form, or for making a mixture suitable for extrusion and spheronisation can easily be determined by trial and error using standard equipment. For example if spheronised pellets are desired the mixture will be too wet if an agglomerate is obtained and will be too dry if the particles disintegrate during spheronisation. Nevertheless wetter or drier mixtures may be suitable for drying to powders which may be used for filling or tabletting to produce dosage forms.

In a preferred embodiment the self-emulsifying system further comprises an active agent. The active agent may be, but is not limited to, a pharmaceutical, veterinary product, agrochemical, pesticide, dye or radiochemical. In particular, it is envisaged that the self-emulsifying system may be used to carry any hydrophobic or water sensitive active agent.

In a further embodiment the first portion further comprises a filler. The filler may be any conventional filling material used in various branches of formulation technology, such as lactose or another sugar. Other common fillers are calcium carbonate and glyceryl monostearate. The filler may be present in an amount of 0 to 75% based on the weight of the microcrystalline cellulose, particularly 0 to 50%.

In particular the present invention is surprisingly useful for providing solid dosage forms of hydrophobic or water sensitive active agents.

Accordingly the present invention comprises a mixture comprising:

I. a first portion comprising microcrystalline cellulose and optionally a filler; and II. a second portion comprising:
  (A) up to 200%, based on the weight of the first portion, of an oily substance;
  (B) between 2 and 100%, based on the weight of the first portion, of a surfactant;
  (C) between 2 and 1000%, based on the weight of the oily substance and the surfactant, of water; and
  (D) between 0.1 and 100%, based on the weight of the oily substance and the surfactant, of an active ingredient;
    wherein the total weight of the oily substance and the surfactant is between 2 and 200% of the first portion; which mixture is dried.

The active ingredient is preferably present in an amount of between 0.5 and 50%, particularly between 2 and 40%, more particularly between 5 and 25%, based on the weight of the oily substance and surfactant.

The mixture is generally dried at about room temperature to about 60° C., depending on the nature of the mixture. The drying should be done below a temperature causing degradation of any of the components. Drying is generally carried out until the mixture loses no more water or at least until the mixture is sufficiently dry to process into a solid dosage form. Drying may be carried out on a tray in an oven or by fluidised-bed drying or other conventional methods.

This drying step may be carried out before or after further processing of the mixture. If carried out before processing the dry mixture may be compressed into tablets or used to fill dosage forms.

Alternatively, before drying the mixture may be extruded by conventional means, for example through a 1 mm die. The extrudate may then be dried and compressed into tablets, or spheronised by conventional means before drying with the resulting pellets optionally being compressed into tablets.

The present invention therefore provides a solid dosage form obtainable by drying a mixture comprising:

I. a first portion comprising microcrystalline cellulose and optionally a filler; and II. a second portion comprising:
  (A) up to 200%, based on the weight of the first portion, of an oily substance;
  (B) between 2 and 100%, based on the weight of the first portion, of a surfactant;
  (C) between 2 and 1000%, based on the weight of the oily substance and the surfactant, of water; and
  (D) between 0.1 and 100%, based on the weight of the oily substance and the surfactant, of an active ingredient;
    wherein the total weight of the oily substance and the surfactant is between 2 and 200% of the first portion.

In particular the dosage form is a tablet or filled capsule. The filled capsule may be made of soft or hard gelatin, particularly hard gelatin.

Thus the present invention provides a process for making a solid dosage form comprising drying a mixture comprising:

I. a first portion comprising microcrystalline cellulose and optionally a filler; and II. a second portion comprising:
  (A) up to 200%, based on the weight of the first portion, of an oily substance;
  (B) between 2 and 100%, based on the weight of the first portion, of a surfactant;
  (C) between 2 and 1000%, based on the weight of the oily substance and the surfactant, of water; and
  (D) between 0.1 and 100%, based on the weight of the oily substance and the surfactant, of an active ingredient;
    wherein the total weight of the oily substance and the surfactant is between 2 and 200% of the first portion; and compressing the dried mixture into a tablet.

There is also provided a process for making a solid dosage form comprising extruding and spheronising a mixture comprising:

I. a first portion comprising microcrystalline cellulose and optionally a filler; and II. a second portion comprising:
  (A) up to 200%, based on the weight of the first portion, of an oily substance;
  (B) between 2 and 100%, based on the weight of the first portion, of a surfactant;
  (C) between 2 and 1000%, based on the weight of the oily substance and the surfactant, of water; and
  (D) between 0.1 and 100%, based on the weight of the oily substance and the surfactant, of an active ingredient;
  wherein the total weight of the oily substance and the surfactant is between 2 and 200% of the first portion;
  drying the spheronised pellets and either filling a capsule with the pellets or compressing the pellets into a tablet.

The same preferred features given above for the mixtures apply to the solid dosage forms also.

The term "spheronised" is intended to refer to pellets which have been processed on spheronisers used in the field of formulation, whether if a suitable size for laboratory or industrial scale processing, or prepared on other devices giving equivalent pellets. Such spheronisers are run at conventional speeds.

Further advantages of the present invention are that the mixture can be extruded at higher pressures than normally possible without clogging or disintegration. Further, the extrudate readily forms spheronised pellets even if the extrudate is prone to initial disintegration. Also the nature of the spheronised pellets is not affected by excess time on the spheroniser after they are formed. Thus the mixture shows excellent handling properties and stability during processing. The dried mixture also demonstrates good stability. In addition the mixtures of the present invention may comprise surprisingly large amounts of oily substance upon addition of a small quantity of water to the wet mixture.

It is understood that self-emulsifying systems other than mono and diglycerides with polysorbate 80 may be used in the present invention, such as those disclosed in WO-A-9119563.

The following Example illustrates the present invention.

EXAMPLE

Microcrystalline cellulose (Avicel® PH 101) (FMC International, Little Island, Cork, Ireland) and lactose (Pharmatose® 200M) (DMV International, Vehgel, The Netherlands) was used as filling and pellet forming material. MP (Mono- and diglycerides USNF (50% w/w)/Polysorbate 80 USNF 50% w/w). Deionized water (W) was used for preparation of MPW.

The experimental design employed in this study was a central composite design with two independent factors and five levels of each factor. This gave a total of 13 experiments, including the centre point and four interaction points (Podczeck, 1996). The independent factors were chosen to be the ratio of lactose to Avicel® and the ratio of MP to water. The responses to be studied were MPW and MP content of the powder mass; extrusion force; median size, size spread, disintegration time, tensile strength, surface roughness and shape of the pellets. The amount of MPW required for each batch was not known and had to be assessed by trial and error. Preliminary experiments were performed to set the limits of the levels of the independent factors. For the composition of the 13 formulations, (Table 1: Quantities of liquid incorporated and the steady state extrusion force). The formulations were produced in random order.

The results were analysed with univariate analysis of variance (ANOVA) to allow identification of statistically significant correlations between the independent factors and the responses, using SPSS 8.0 for Windows (Podczek, 1996).

MPW mixtures were prepared by adding the MP to the water and stirring with a magnetic stirrer for 10 minutes. The mixtures were used on the same day as they were prepared.

Avicel® and lactose (50 g total) were pre-blended with a pestle and mortar and wetted by gradual addition of MPW. Extrusion was carried out with a ram extruder (Lloyd MX50) with a die of 1 mm in diameter and 6 mm in length, extrusion speed 200 mm/minute. A force/displacement curve was obtained for each extrusion to allow determination of the extrusion force. The extrudate was spheronized for 10 minutes on a 120 mm diameter spheronizer (Caleva) using a cross-hatch friction plate with speed of 1880 rpm. The resulting pellets were dried in an oven at 40° C. until they reached constant weight.

Size analysis was performed using a nest of British standard sieves (500, 710, 1000, 1400, 2000, 2800, 4000 and 5600 $\mu$m aperture) agitated on a sieve shaker for 10 minutes. Retained weight data were used to construct cumulative % undersize distributions. Median diameter and spread was determined as the 50% value and the difference between 99% and 1%.

The disintegration of the pellets was studied in deionized water at 37° C. using a disintegration apparatus (BP 1998, modified with a 1 mm mesh at the base of the tubes). Six pellets from each batch were tested. The end point was taken as the time for disruption of the pellets.

The crushing strength of the pellets was analysed using a CT5 tester (Engineering Systems, Nottingham, UK) with a 5 kg load cell and a speed of 10 mm/minute. A random sample of 10 pellets was tested. The crushing load was converted into surface tensile stress using the following equation (Shipway and Hutchings. 1993):

$$\sigma_f = (0.4 F_0)/(\Pi R^2)$$

where $\sigma_f$ is the surface tensile stress [N/m$^2$], F is the crushing load [N] and R is the radius [m]. The radius was calculated from the Feret diameter.

The shape of the pellets was studied by image analysis using a Seescan Image Analyser (Seescan, Cambridge, UK), completed with a black and white camera (CCD-4 miniature video camera module, Rengo Co. Ltd. Toyohashi, Japan) connected to a zoom lens (18-108/2.5, Olympus, Hamburg, Germany). A shape factor, to describe the roundness of the pellets, and the Feret diameter was determined by analysing a random sample of 100 pellets from each batch. (Podczeck and Newton, 1994: Podczeck and Newton, 1995).

The surface roughness of the pellets was studied using a non-contacting laser profilometer (UBM Microfocus Measurement System, UBM Messtechnik GmbH, Ettlingen, Germany) with a light spot diameter of 1 $\mu$m and a measurement range of ±500 $\mu$m. The area scanned was 0.3×0.3 mm with a resolution of 1000 points/mm in both directions. Scans were levelled to remove any underlying slope or curvature. The UBSOFT (UBM Messtechnik GmbH, Ettlingen,. Germany) associated with the laser profilometer system was used to determine four different roughness parameters: Ra, Rq, Rtm and fractal dimension (Podezeck, 1998). Five pellets from each batch was studied.

The amount of MPW required for each formulation was not known and had to be assessed by trial and error until a 'good' product without any apparent agglomerates was formed. If the formulation gave agglomerates the amount of MPW was lowered. Some formulations gave a good product on the first attempt. In total 25 batches were produced (Table 1). After sieving the 'best' batch from each formulation was chosen for further analysis. Batches with pellets larger than 2800 µm were excluded (Table 2: Retained weight (g) of pellets in the size fractions).

According to the model equation and assuming that all the water evaporated, the maximum amount of MP that could be incorporated was 36 g (MP:water ratio 92:8, lactose:Avicel® ratio 0:100), which is 42% of dry pellet weight.

Statistical analysis of the extrusion forces showed a linear relationship with the MP:water ratio, the more MP the higher extrusion force. The lactose:Avicel® ratio had no statistically significant influence. As for the spheronization process formulation number 9 seemed to have a different mechanism of spheronization than what has been proposed (Chapman, 1985). The extrudate first broke into powder and pellets started to form after a few minutes. With many of the formulations some powder was stuck on the plate after the spheronization. This can be a problem in pharmaceutical production when batch after batch is loaded onto the spheronizer.

Both parameters describing the pellet size distribution, median diameter and size spread, were found to be dependent on the MP:water ratio (Table 3: Results of the size analysis). The median diameter increases with increased amount of MP and levels off. The size spread has a linear relationship with the MP:water ratio and increases with increased amount of MP. No statistically significant correlation with the lactose:Avicel® ratio could be found.

Statistical analysis of the disintegration results showed a cubic correlation between disintegration time and MP:water ratio in size fraction 1000–1400 µm, values are mean for 6 pellets (Table 4). The disintegration time increases dramatically when the water content is increased from 70% to 100%. The lactose:Avicel® ratio had no statistically significant influence (Table 5: Crushing load on pellets in size fractions 710–1000 µm and 1000–1400 µm, values are mean of 10 pellets).

The surface tensile stress was studied in two size fractions. Statistical analysis of the results showed a quadratic relationship between tensile stress and the MP:water ratio for both size fractions. The lactose:Avicel® ratio had a small influence on the tensile stress in size fraction 710–1000 µm but no effect in size fraction 1000–1400 µm. Reasons for this difference could be that the pellets are formed in different ways or have a different composition, which could affect the mechanical properties. Some of the pellets, those with a MP content of 60% or more, did not snap, but were squashed between the platens. They deformed plastically, yet there was a yield load.

Statistical analysis of the shape factor showed that there was no statistically significant correlation with either of the two independent factors (Table 6: shape factors (Ecc) for the pellets in size fractions 710–1000 µm and 1000–1400 µm. Values are mean of 100 pellets). This means that there is no systematic change in shape as the independent factors are varied.

The surface roughness is presented as maximum peak to Valley height for size fraction 1000–1400 µm (Table 7). Rtm. Oneway ANOVA showed that this parameter would be best to describe the surface roughness. Statistical analysis showed that Rtm was dependent on both the MP:water ratio and the lactose:Avicel® ratio. The roughness has a minimum and according to the model equation the smoothest pellets would be made of 100% Avicel® and MPW with 59% MP.

REFERENCES

Chapman S. R., Influence or process variables on the production of spherical particles. *Ph.D. Thesis.* University of London (1985) p. 281.

Podczeck F., The development and optimization of tablet formulations using mathematical methods. In Alderborn G. and Nyström C., (Eds.). *Pharmaceutical Powder Compaction Technology*, Marcel Dekker Inc., New York, 1996, pp. 561–593.

Podczeck F., Particle-particle adhesion in pharmaceutical powder handling. Imperial College Press, London, 1998, pp. 16–28.

Podczeck F. and Newton J. M., A shape factor to characterize the quality of spheroids. *J. Pharm. Pharmacol.,* 46 (1994) 82–85.

Podczeck F. and Newton J. M., The evaluation of a three-dimensional shape factor for the quantitative assessment of the sphericity and surface roughness of pellets. *Int. J. Pharm.,* 124 (1995) 253–259.

Shipway P. H. and Hutchings I. M., Attrition of brittle spheres by fraction under compression and impact loading. *Powder Technol.,* 76 (1993) 23–30.

What is claimed is:

1. A self-emulsifying system which comprises:
   I. a first portion comprising microcrystalline cellulose; and
   II. a second portion comprising:
   (A) up to 200%, based on the weight of the first portion, of an oily substance;
   (B) between 2 and 100%, based on the weight of the first portion, of a surfactant; and
   (C) between 2 and 1000%, based on the weight of the oily substance and the surfactants, of water;
   wherein the total weight of the oily substance and the surfactant is between 2 and 200% of the first portion.

2. A self-emulsifying system according to claim 1 wherein the amount of oily substance present is between 20 and 42% of the weight of the first portion.

3. A self-emulsifying system according to claim 1 wherein the amount of surfactant present is between 20 and 50% of the weight of the first portion.

4. A self-emulsifying system according to claim 1 wherein the amount of water present is between 8 and 42% of the weight of oil and surfactant.

5. A self-emulsifying system according to claim 1 wherein the combined weight of the second portion is between 40 and 90% by weight of the first portion.

6. A self-emulsifying system according to claim 1 which further comprises between 0.1 and 100%, based on the weight of the oily substance and the surfactant, of an active ingredient optionally chosen from a pharmaceutical, veterinary product, agrochemical pesticide, dye and a radiochemical.

7. A self-emulsifying system according to claim 1 wherein the first portion further comprises a filler in an amount of 0 to 75% based on the weight of the microcrystalline cellulose.

8. A self-emulsifying system according to claim 1 wherein the surfactant is polysorbate 80 or a mixture thereof with span 80.

9. A self-emulsifying system according to claim 1 wherein the combination of oily substance and surfactant is mono and diglycerides USNF (50% w/w) and polysorbate 80 NF (50% w/w); mono and diglycerides USNF (70% w/w), polysorbate 80 NF (20% w/w) and span 80 (10% w/w); or soyabean oil (30%) w/w, polysorbate 80 NF (49% w/w) and span 80 (21% w/w).

10. A mixture comprising:
   I. a first portion comprising microcrystalline cellulose and optionally a filler; and
   II. a second portion comprising:
   (A) up to 200%, based on the weight of the first portion, of an oily substance;

(B) between 2 and 100%, based on the weight of the first portion, of a surfactant;
(C) between 2 and 1000%, based on the weight of the oily substance and the surfactant, of water; and
(D) between 0.1 and 100%, based on the weight of the oily substance and the surfactant, of an active ingredient;

wherein the total weight of the oily substance and the surfactant is between 2 and 200% of the first portion; which mixture is dried.

11. The mixture of claim 10 wherein the active ingredient is present in an amount of between 5 and 25% based on the weight of the oily substance and surfactant.

12. A solid dosage form obtainable by drying a mixture comprising:

I. a first portion comprising microcrystalline cellulose and optionally a filler; and II. a second portion comprising:
(A) up to 200%, based on the weight of the first portion, of an oily substance;
(B) between 2 and 100%, based on the weight of the first portion, of a surfactant;
(C) between 2 and 1000%, based on the weight of the oily substance and the surfactant, of water; and
(D) between 0.1 and 100%, based on the weight of the oily substance and the surfactant, of an active ingredient;

wherein the total weight of the oily substance and the surfactant is between 2 and 200% of the first portion.

13. A process for making a solid dosage form comprising drying a mixture comprising:

I. a first portion comprising microcrystalline cellulose and optionally a filler; and II. a second portion comprising:
(A) up to 200%, based on the weight of the first portion, of an oily substance;
(B) between 2 and 100%, based on the weight of the first portion, of a surfactant;
(C) between 2 and 1000%, based on the weight of the oily substance and the surfactant, of water; and
(D) between 0.1 and 100%, based on the weight of the oily substance and the surfactant, of an active ingredient;

wherein the total weight of the oily substance and the surfactant is between 2 and 200% of the first portion; and compressing the dried mixture into a tablet.

14. A process for making a solid dosage form comprising extruding and spheronising a mixture comprising:

I. a first portion comprising microcrystalline cellulose and optionally a filler; and II. a second portion comprising:
(A) up to 200%, based on the weight of the first portion, of an oily substance;
(B) between 2 and 100%, based on the weight of the first portion, of a surfactant;
(C) between 2 and 1000%, based on the weight of the oily substance and the surfactant, of water; and
(D) between 0.1 and 100%, based on the weight of the oily substance and the surfactant, of an active ingredient;

wherein the total weight of the oily substance and the surfactant is between 2 and 200% of the first portion; drying the spheronised pellets and either filling a capsule with the pellets or compressing the pellets into a tablet.

* * * * *